US005460609A

United States Patent [19]
O'Donnell

[11] Patent Number: 5,460,609
[45] Date of Patent: Oct. 24, 1995

[54] ELECTROMECHANICAL INFLATION/DEFLATION SYSTEM

[75] Inventor: Joseph A. O'Donnell, Escondido, Calif.

[73] Assignee: Advanced Cardiovascular Systems, Inc., Santa Clara, Calif.

[21] Appl. No.: 156,254

[22] Filed: Nov. 22, 1993

[51] Int. Cl.⁶ .............................. A61M 29/00; A61M 1/00
[52] U.S. Cl. .............................................. 604/100; 604/121
[58] Field of Search .............................. 604/97–100, 121, 604/152

[56] References Cited

U.S. PATENT DOCUMENTS

| | | |
|---|---|---|
| 3,623,474 | 11/1971 | Heilman . |
| 3,698,381 | 10/1972 | Federico et al. . |
| 3,701,345 | 10/1972 | Heilman et al. . |
| 3,720,199 | 3/1973 | Rishton et al. . |
| 3,985,123 | 10/1976 | Herzlinger et al. . |
| 4,006,736 | 2/1977 | Kranys et al. . |
| 4,056,043 | 11/1977 | Sriramamurty et al. . |
| 4,106,002 | 8/1978 | Hogue, Jr. . |
| 4,231,715 | 11/1980 | Gleichner .................. 417/307 |
| 4,332,254 | 6/1982 | Lundquist . |
| 4,370,982 | 2/1983 | Reilly . |
| 4,439,185 | 3/1984 | Lundquist . |
| 4,439,186 | 3/1984 | Kuhl . |
| 4,444,335 | 4/1984 | Wood et al. . |
| 4,493,704 | 1/1985 | Beard et al. . |
| 4,576,181 | 3/1986 | Wallace et al. . |
| 4,583,917 | 4/1986 | Shah . |
| 4,583,974 | 4/1986 | Kokernak . |
| 4,608,994 | 9/1986 | Ozawa et al. . |
| 4,610,256 | 9/1986 | Wallace . |
| 4,651,738 | 3/1987 | Demer et al. . |
| 4,654,027 | 3/1987 | Dragan et al. . |
| 4,655,749 | 4/1987 | Fischione . |
| 4,677,980 | 7/1987 | Reilly et al. . |
| 4,677,982 | 7/1987 | Llinas et al. . |
| 4,694,409 | 7/1987 | Lehman . |
| 4,723,938 | 2/1988 | Goodin et al. . |
| 4,743,230 | 5/1988 | Nordquest . |
| 4,758,223 | 7/1988 | Rydell . |
| 4,781,192 | 11/1988 | Demer . |
| 4,795,431 | 1/1989 | Walling . |
| 4,796,606 | 1/1989 | Mushika . |
| 4,808,165 | 2/1989 | Carr . |
| 4,832,692 | 5/1989 | Box et al. . |
| 4,838,864 | 6/1989 | Peterson . |
| 4,854,324 | 8/1989 | Hirschman et al. . |
| 4,872,483 | 10/1989 | Shah .......................................... 137/557 |
| 4,911,695 | 3/1990 | Lindner . |
| 4,919,121 | 4/1990 | Rydell et al. . |
| 4,929,238 | 5/1990 | Baum . |
| 4,940,459 | 7/1990 | Noce . |
| 4,944,726 | 7/1990 | Hilal et al. . |
| 4,952,928 | 8/1990 | Carroll et al. . |
| 4,985,015 | 1/1991 | Obermann et al. . |
| 5,004,472 | 4/1991 | Wallace . |
| 5,007,904 | 4/1991 | Densmore et al. . |
| 5,009,662 | 4/1991 | Wallace et al. ........................ 606/192 |
| 5,015,233 | 5/1991 | McGough et al. . |
| 5,019,041 | 5/1991 | Robinson et al. . |
| 5,021,046 | 6/1991 | Wallace . |
| 5,047,015 | 9/1991 | Foote et al. . |

(List continued on next page.)

FOREIGN PATENT DOCUMENTS

| | | |
|---|---|---|
| WO90/04987 | 5/1990 | WIPO . |
| WO90/11040 | 10/1990 | WIPO . |
| WO92/06735 | 4/1992 | WIPO . |
| WO92/15359 | 9/1992 | WIPO . |

Primary Examiner—John D. Yasko
Assistant Examiner—Adam J. Cermak
Attorney, Agent, or Firm—Fulwider Patton Lee & Utecht

[57] ABSTRACT

An automated inflation/deflation system for use in connection with a dilatation balloon catheter in vascular procedures that greatly facilitates the operator's control of the inflation or deflation of the balloon and control of maneuvering the proximal end of the catheter for proper positioning of the balloon inside the patient's vasculature. By use of a pressure transducer and a display unit, the operator can monitor information relating to inflation pressure and inflation time. In addition, the system provides for safety features for effectuating a rapid reduction in balloon pressure.

5 Claims, 2 Drawing Sheets

U.S. PATENT DOCUMENTS

| | | |
|---|---|---|
| 5,057,078 | 10/1991 | Foote et al. . |
| 5,084,060 | 1/1992 | Freund et al. . |
| 5,135,488 | 8/1992 | Foote et al. .............................. 604/97 |
| 5,152,776 | 10/1992 | Pinchuk . |
| 5,163,904 | 11/1992 | Lampropoulos et al. . |
| 5,201,753 | 4/1993 | Lampropoulos et al. . |
| 5,215,523 | 6/1993 | Williams et al. ......................... 604/97 |
| 5,218,970 | 6/1993 | Turnbull et al. ........................ 128/748 |
| 5,259,838 | 11/1993 | Taylor et al. ............................. 604/97 |
| 5,273,537 | 12/1993 | Haskuitz et al. ......................... 604/99 |

ELECTROMECHANICAL INFLATION/DEFLATION SYSTEM

BACKGROUND OF THE INVENTION

This invention generally relates to inflation devices used in medical procedures. More particularly, the present invention pertains to inflation control systems suitable for inflating and deflating catheter balloons used in vascular procedures such as angioplasty performed on a patient for maintaining the patency of a blood vessel.

Dilatation balloon catheters have been used in increasing numbers in angioplasty procedures to dilate or enlarge blood vessels that have been partially or almost completely blocked by stenosis (a narrowing of the vessel due to injury or disease). Angioplasty procedures have been used to treat stenoses in coronary arteries, peripheral arteries, urethral passages, fallopian tubes, etc. Particularly, the procedure for dilating coronary arteries, referred to as percutaneous transluminal coronary angioplasty (PTCA), has provided an effective and less traumatic treatment technique than coronary by-pass surgery or other surgical treatment methods.

In a typical angioplasty procedure, a guiding catheter is percutaneously introduced into the vascular system of a patient and is directed to a point near the site of the occlusion. Subsequently, a guidewire and a dilatation catheter having an inflatable balloon on the distal end thereof are introduced through the guiding catheter with the guidewire slidably disposed within an inner lumen of the dilatation catheter. The guidewire is advanced out of the distal end of the guiding catheter and is maneuvered into the patient's vasculature containing the lesion to be dilated, and is then advanced beyond the lesion. Thereafter, the dilatation catheter is advanced over the guidewire until the dilatation balloon is located across the lesion. Once in position across the lesion, the balloon of the dilatation catheter is filled with radiopaque liquid at relatively high pressures (e.g., generally greater than about 4 atmospheres) and is inflated to a predetermined size, preferably the same as the inner diameter of the artery at that location. The inflated balloon radially compresses the atherosclerotic plaque of the lesion against the inside of the artery wall to thereby dilate the lumen of the artery and allow blood to flow freely therethrough. In a typical PTCA procedure, the balloon is inflated and deflated several times, with the pressure maintained for several seconds during each inflation, until the desired patency in the blood vessel is obtained. The balloon is then deflated so that the dilatation catheter can be removed and blood flow resumed through the dilated artery.

To inflate or deflate the balloon, the physician typically uses an inflation system such as a syringe placed in fluid communication with the interior of the balloon. The physician uses one hand to grasp the syringe body and the other hand to maneuver the plunger to pressurize or depressurize the inflation fluid as required. Syringe-type inflation systems of the type described are manufactured and sold by Advanced Cardiovascular Systems, Inc. of Santa Clara, Calif. under the trademark INDEFLATOR.

There are some drawbacks associated with a manual inflation procedure such as the one described. For example, each time the physician wants to adjust or change the location of the balloon in the artery, she must use her hands alternatingly on the proximal end of the catheter for maneuvering the balloon to the desired location and on the inflation device for pressurizing or depressurizing the balloon. Rather than switching hands between the balloon catheter and the inflation device, it is desirable for the physician to be able to simultaneously control the inflation pressure and the location of the balloon in the artery. Another drawback of manual inflation systems is that the physician may experience hand fatigue as a result of operating an inflation device for several inflation and deflation cycles, each lasting several seconds, during an angioplasty procedure. Additionally, manual inflation devices are typically bulkier than dilatation balloon catheters, and the presence of such a bulky instrument is preferably to be avoided in the immediate area of an angioplasty procedure.

In addition to the above concerns, it is desirable for the physician performing an angioplasty procedure to monitor the balloon pressure and the time of inflation. A balloon pressure display allows the physician to monitor whether the arterial plaque causing the stenosis is subjected to a sufficiently high pressure to cause compression of the plaque. Also, the physician would like to monitor the balloon pressure to ensure that the balloon pressure limits specified by the manufacturer are not exceeded so as to cause balloon failure, and in case the balloon pressure suddenly changes, the pressure display can alert the physician of the possibility of some failure either of the artery or of the catheter itself. Furthermore, it is desirable for the physician to monitor the elapsed time of each inflation and the time between inflations so as not to deprive the patient of blood flow inside the artery beyond acceptable time periods. Early model inflation systems provided balloon pressure measurements by utilizing analog pressure gauges to correlate the force applied on the inflation device with the pressure inside the balloon.

In recent years, various inflation devices have become known which are able to instantaneously monitor, display, and record balloon pressure values and inflation times. Other advances in the design of inflation systems have been directed to creating automated inflation devices, whereby a microprocessor provides control signals to a drive unit which advances or retracts the plunger of a syringe containing inflation fluid for the purpose of inflating or deflating a balloon catheter. The microprocessor can be made to follow a predetermined output pattern based on the inflation pressure detected by the pressure transducer and the duration of inflation, or it can be designed for manual activation by control switches that are typically mounted on the same unit that displays the pressure and time values. One automated inflation device includes a floor switch for operating a timer for measuring the duration of inflation and deflation of the balloon. However, there are some disadvantages in connection with the use of floor switches, such as the possibility of having catheter lab personnel inadvertently stepping on the floor switch. Also, floor switches accidentally may be kicked out of reach and may be subjected to contamination by spilled fluids.

Further, such existing inflation devices reduce the hands-on control of a physician who may desire to inflate or deflate the balloon catheter at a precise and desirable moment during the maneuvering of the catheter in the artery. Activation of control switches that are typically mounted away from the balloon catheter requires the physician to give up control of the proximal end of the catheter in order to activate the control switches. Thus, existing inflation systems do not lend themselves to easy activation of the inflation device by the physician at the same time as he or she is maneuvering the balloon catheter into position in the patient's vasculature.

What has been needed and heretofore unavailable is a simplified automated inflation/deflation system that enables the physician to effectively, easily, and simultaneously control the inflation pressure and the maneuvering of the balloon catheter. The control switch would be properly located so as to enable the physician to achieve such effective, easy, and simultaneous control. Such an inflation/ deflation system would be able to easily interface with commercially available dilatation balloon catheters, and would eliminate the need for having bulky components of an inflation system in the immediate area of an angioplasty procedure. Also, such an automated inflation/deflation system would be able to monitor and display information relating to balloon pressure and inflation times at one or more convenient display locations. Lastly, it would be very desirable for such an inflation system to have a safety feature for quickly deflating the balloon in an emergency such as the appearance of a small leak in the balloon or the patient having an adverse reaction to the blockage of blood flow caused by the inflation of the balloon. The present invention fulfills these needs.

SUMMARY OF THE INVENTION

The invention is directed to an inflation/deflation system for effectuating the inflation and deflation of a dilatation balloon catheter used in vascular procedures such as angioplasty. The present invention allows the physician to maintain control of the balloon pressure simultaneously as he or she is positioning the catheter in a desired location inside the patient's vascular system. The invention further provides a safety feature that allows the physician to reduce the balloon pressure quickly in an emergency situation. In addition, the present system eliminates hand-fatigue experienced by the use of manually operated inflation devices, and also eliminates the need for having a bulky inflation device in the immediate area of the vascular procedure. Further, the invention allows information relating to the pressure and inflation times to be displayed at one or more convenient locations.

The inflation/deflation system in accordance with the present invention includes a fluid chamber having a plunger for pressurizing a body of inflation fluid in response to the movement of the plunger that is caused by an electromechanical motor drive unit. The motor drive unit itself is activated in response to a signal directed from a control switch which is easily accessible to the physician.

Upon the movement of the plunger distally inside the fluid chamber, the inflation fluid is directed towards the inflation lumen of a balloon catheter via a tubing that runs between the distal end of the fluid chamber and the proximal end of the catheter's inflation lumen. As the catheter's inflation lumen is open to the interior of the balloon (or inflatable region), the inflation fluid travels through the inflation lumen and enters the balloon region and inflates the balloon.

After each expansion of the balloon or inflatable region, the deflation of the balloon region takes place by either slowly or rapidly reversing the movement of the motor drive unit so as to withdraw the inflation fluid from the interior of the balloon region and direct it back to the fluid chamber. In order to make it possible for the physician to depressurize the balloon region in case of any failures of the motor drive unit or other emergency situations, the fluid chamber is designed so that it may also be manually withdrawn from the system by the physician. Also, the plunger is designed so that it can be grasped by the physician and withdrawn from the fluid chamber to create a vacuum.

For ease of access and control by the physician, the control switch is mounted on or is secured to the tubing close to the proximal end of the balloon catheter. The proximity of the control switch to the proximal end of the catheter allows the physician to keep one hand on the proximal end of the catheter for maneuvering the catheter while using his other hand on the control switch for effectuating the inflation or deflation of the balloon region. Thus, increased accessibility to the control switch greatly facilitates the physician's task in positioning and inflating the balloon region of the catheter at the site of the stenosis. Also, the improved accessibility of the control switch allows the physician to effectuate a rapid deflation of the balloon whenever necessary.

The control switch may communicate with the motor drive unit via electrically conductive wires or radiation waves (e.g., infrared or radio frequency radiation). In the case of communication by radiation waves, the control switch may be in the form of a remote control unit that can be separate as well as attachable to a specific location, such as the tubing between the fluid chamber and the inflation lumen of the catheter.

If desired, the present invention also may provide for a backup switch located on the motor drive unit or on a separate display unit. In case of failure (or misplacement) of the primary control switch, this backup switch would be operable to activate the motor drive unit in a similar fashion as the primary control switch (i.e., via electrically conductive wires or radiation waves).

The inflation/deflation system of the invention provides the ability to monitor the balloon pressure and the duration of inflation. For this purpose, a pressure transducer is placed at or near the proximal end of the tubing in fluid communication with the inflation fluid. Upon exposure to the fluid, the pressure transducer communicates a signal that is indicative of the balloon pressure to a display unit. The display unit may also display the duration of each inflation and the time between inflations. Display of such information related to the inflation or deflation of the balloon may be displayed on a portion of the control switch, or alternatively, on a unit which may be placed either with the motor drive unit or a completely separate display unit. Also, for ease of use, display of the desirable information may take place at more than one location. For example, the pressure and inflation times may be displayed both on the separate display unit as well as on the control switch.

The control switch of the present invention can be made for single-use applications. Alternatively, in order to lower the cost associated with the present invention, the control switch of the invention can be placed in a sterile, disposable cover during each application so that it may be reused in future applications on various patients.

The present invention allows for the detection of the presence of the fluid chamber and the pressure transducer in the system by providing for electrical connectors on the fluid chamber and the pressure transducer that mate with matching connectors in the system. The present invention also allows for the installation of the fluid chamber in an orientation with the fluid chamber outlet located at a higher elevation than the plunger so that air bubbles may rise to the upper end of the fluid chamber (towards its outlet) and be easily seen and ejected from the system.

These and other advantages of the invention will become more apparent from the following detailed description thereof when taken in conjunction with the accompanying exemplary drawings.

DETAILED DESCRIPTION OF THE INVENTION

Figure 1:
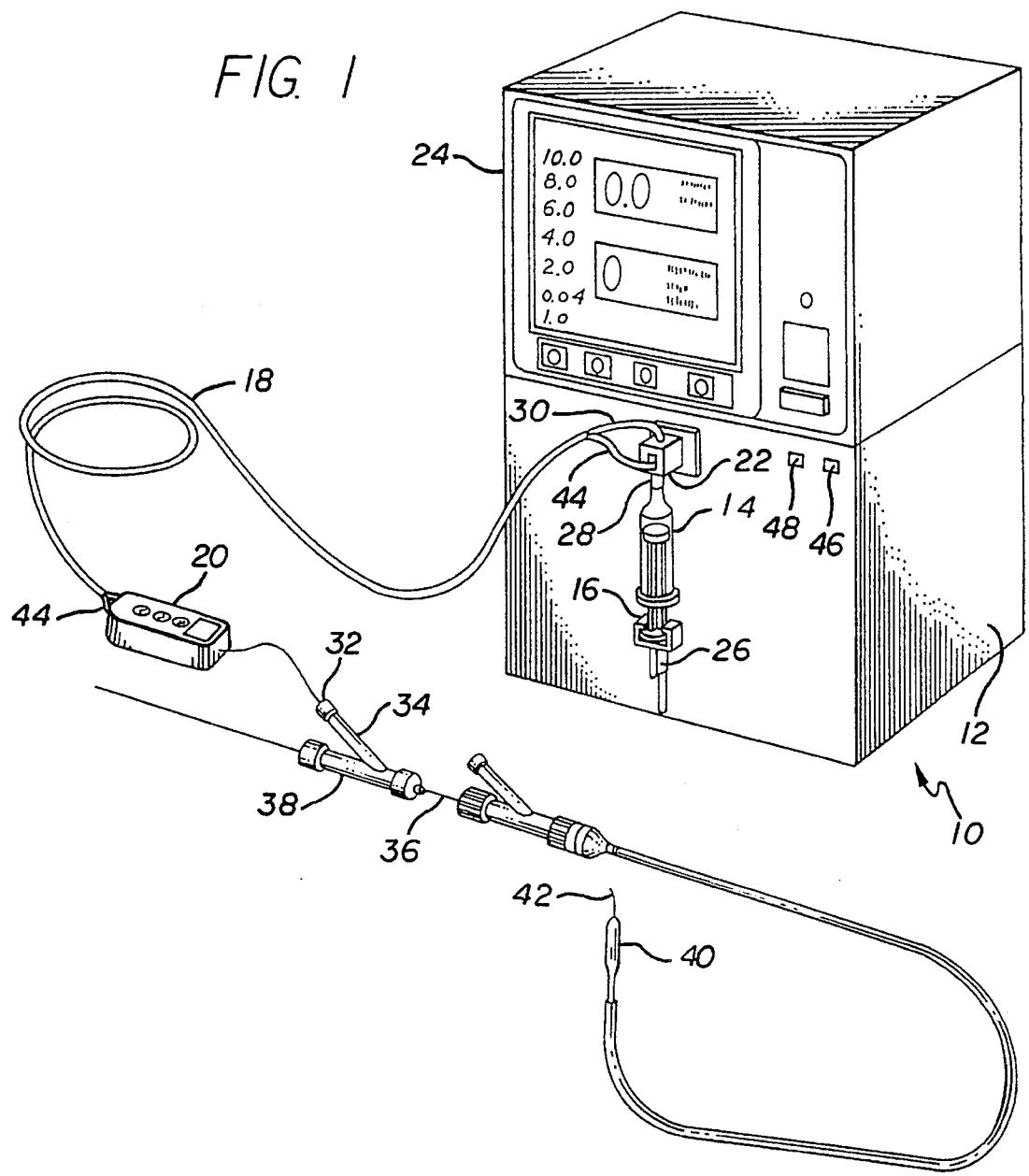
FIG. 1 is a schematic drawing of an inflation/deflation system embodying features of the invention.
Figure 2:
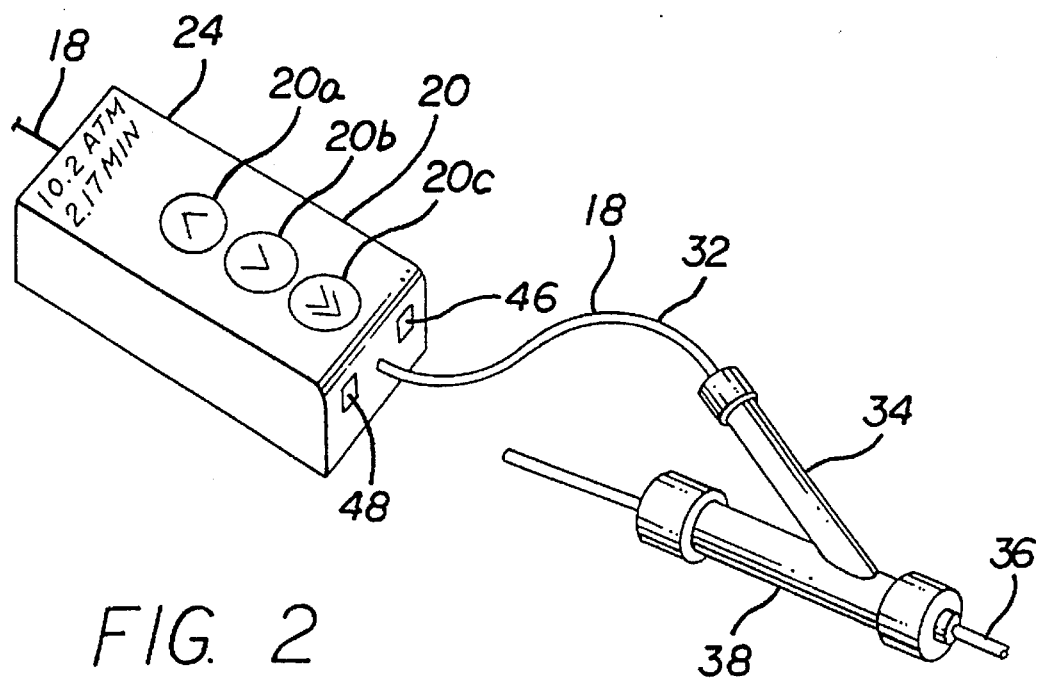
FIG. 2 is a schematic of the control switch of the inflation/deflation system shown in FIG. 1, mounted in close proximity of the proximal end of the catheter, and incorporating a display unit for displaying balloon pressure and inflation times.

FIGS. 1 and 2 illustrate in schematic form an inflation/deflation system 10 embodying features of the invention. Inflation/deflation system 10 generally includes an electromechanical motor drive unit 12, a fluid chamber 14 with a plunger 16, a tubing 18, a control switch 20, a pressure transducer 22, and a display unit 24.

Electromechanical motor drive unit 12 may be in the form of a stepper motor, a DC servo motor, a hydraulic motor, a pneumatic motor, or the like. Whatever the specific type, motor drive unit 12 typically has a moveable arm 26 that is capable of directing the movement of another element, such as by pushing or pulling, that it may come in contact with. As shown in FIG. 1, arm 26 is connected to plunger 16 of fluid chamber 14. Fluid chamber 14 may be mounted in an orientation wherein fluid chamber outlet 28 is located at a higher elevation than plunger 16. Preferably, fluid chamber 14 is mounted in a vertical orientation with fluid chamber outlet 28 at the top and plunger 16 at the bottom. This arrangement enhances the system's capability for eliminating air bubbles that rise to the top. Fluid chamber 14 and plunger 16 may be formed of a typical syringe/plunger combination with an O-ring or quad seal or with a rolling diaphragm seal for reduced friction. Other suitable means that can pressurize (or depressurize) and direct a quantity of fluid may also be used.

As arm 26 forces plunger 16 inside fluid chamber 14, the inflation fluid inside fluid chamber 14 is pressurized, and is directed out of fluid chamber outlet 28. The reverse movement of arm 26 reduces the pressure of the inflation fluid, and directs the fluid back inside the fluid chamber. A length of tubing 18 has its proximal end 30 connected to outlet 28 and its distal end 32 connected to the inflation lumen 34 of a balloon dilatation catheter 36. Inflation lumen 34 extends from the proximal end 38 of dilatation catheter 36 and is in fluid communication with the interior of inflatable region (or balloon) 40 located at or near the distal end 42 of dilatation catheter 36. Accordingly, tubing 18 provides fluid communication between the interior of inflatable region 40 and the inflation fluid inside fluid chamber 14. Tubing 18 may be made of any suitable material that can withstand the pressures associated with the inflation and deflation of a balloon catheter. The preferred material suitable for the tubing is polyurethane with a braided nylon. Other possible materials are PVC or flexible copolymers.

Control switch 20 activates motor drive unit 12 so that arm 26 of motor drive unit 12 applies force on plunger 16 of fluid chamber 14 and pressurizes the inflation fluid inside fluid chamber 14. Upon pressurization, the inflation fluid travels inside tubing 18 and flows into inflatable region 40 via inflation lumen 34 of dilatation catheter 36. As can be seen in FIG. 1, control switch 20 is mounted near distal end 32 of tubing 18 in close proximity with proximal end 38 of dilatation catheter 36. The preferable distance between control switch 20 and proximal end 38 of dilatation catheter 36 is approximately eighteen inches. This distance is selected so that control switch 20 can be operated either by the physician who also is maneuvering the proximal end of the catheter as well as by a technician who may stand close to the physician without interfering with the physician's handling of the proximal end of the catheter. Once inflatable region 40 is properly situated at the site of the stenosis, the physician may use one hand to activate control switch 20 to effectuate the inflation or deflation of inflatable region 40 and the other hand on the proximal end of dilatation catheter 36 to control the location of inflatable region 40.

Control switch 20 may be a rocker switch, a slide switch, a rotary switch, a pressure sensitive switch with tactile feedback, a non-electrical pneumatic control switch, or any other type of switch that may activate and deactivate motor drive unit 12. Control switch 20 may also include an audible feedback system to notify the user of its activation.

Figure 3:
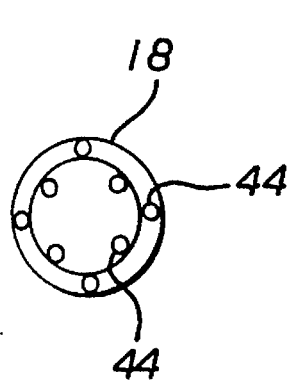
FIG. 3 is a cross-sectional view of the tubing and electrical wires connecting the control switch to the display unit and plunger.
Figure 4:
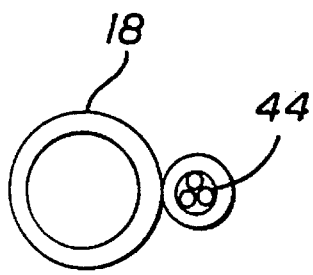
FIG. 4 is a cross-sectional view of an alternative embodiment of the components of FIG. 3.

Control switch 20 preferably includes three individual switches; an increase-pressure switch 20a, a decrease-pressure switch 20b, and a rapid-decrease-pressure switch 20c. In one form of operation, pressure-increase switch 20a is released, after initially being depressed, to pressurize inflatable region 40. After inflatable region 40 is fully pressurized to a level selected by the physician, it remains fully inflated for a period of time. Thereafter, decrease-pressure switch 20b is depressed to decrease pressure in inflatable region 40. The pressure in inflatable region 40 will continue to decrease until it reaches zero, or to a value slightly less than zero atmospheres. Should a situation arise that would necessitate a quick deflation and removal of inflatable region 40 from the patient's artery, rapid-decrease-pressure switch 20c is activated to rapidly decrease the pressure in inflatable region 40 to a predetermined level, usually zero atmospheres or slightly less. The difference between activated decrease-pressure switch 20b and rapid-decrease-pressure switch 20c is that decrease-pressure switch 20b provides a deflation pressure at a predetermined rate, while rapid-decrease-pressure switch 20c provides full current to motor drive unit 12 to cause pressure in the system to rapidly decrease to full vacuum. Several methods of communication between control switch 20 and motor drive unit 12 may be utilized. For example, as shown in FIG. 1, one method of such communication is by using electrical wires 44 routed between control switch 20 and motor drive unit 12. Accordingly, electrical wires 44 may be routed between control switch 20 and motor drive unit 12, while tubing 18 that carries the inflation fluid runs through control switch 20. Under this method, control switch 20 does not perform any function on tubing 18, and it is only being confined to the tubing by making the tubing run through it. As another alternative, as shown in FIG. 3, the control switch may be confined to the tubing and may communicate with the motor drive unit by having electrical wires 44 placed inside or embedded in the wall of tubing 18. As another alternative, as depicted in FIG. 4, electrical wires 44 can be carried in a separate bundle alongside tubing 18.

Another method of communication between control switch 20 and motor drive unit 12 includes the use of electromagnetic radiation waves. For example, as shown in FIGS. 1 and 2, control switch 20 can be provided with transmitter 46 and motor drive unit can be provided with receiver 48 suitable for sending and receiving infrared waves or radio frequency waves. For a two-way communication, as shown in FIGS. 1 and 2, control switch 20 and motor drive unit 12 can each be provided with transmitter and receiver units.

In order to monitor the pressure inside inflatable region 40, pressure transducer 22 (e.g., a piezo-resistive transducer sensitive to changes in pressure) is positioned in the system so that it is in communication with the inflation fluid. The preferred position for pressure transducer 22 is shown in FIG. 1 at or near the proximal end 30 of tubing 18 in communication with the inflation fluid therein. Other types of pressure transducers may be used as long as they are located such that they are capable of sensing the inflation fluid. As another example, a force transducer (not shown) may be placed in line with arm 26 of motor drive unit 12 to measure the force it exerts on plunger 16 of fluid chamber 14. This force could be converted by appropriate means into a measurement of the pressure of the inflation fluid.

The signal indicative of balloon pressure as measured by pressure transducer 22 is directed to display unit 24 which processes the signal and displays it in analog, or preferably, in digital form. In addition, a signal indicative of the movement of motor drive unit 12 or plunger 16 at the start of each inflation and deflation cycle is provided to display unit 24 so that the physician may monitor the duration of each inflation or deflation and the cumulative elapsed time of inflation. As shown in FIG. 1, display unit 24 is preferably located on motor drive unit 12, but may also be placed at a convenient location for easy viewing (e.g., on control switch 20 as shown in FIG. 2, near other x-ray screens, or on a separately located unit). Also, the desired information may be displayed at a combination of such locations.

In addition to the above features, as an added safety feature, plunger 16 is designed to enable the physician to manually grasp it for retraction to thereby rapidly deflate inflatable region 40. As another safety feature, fluid chamber 14 is designed so that the physician may manually remove it from the system. Such actions for manual deflation of the inflatable region may be necessary in various emergency situations such as a power failure or a failure in one of the components of the system. Furthermore, in the present invention, as shown in FIG. 1, the fluid chamber and the plunger are placed in a vertical orientation so as to allow the air bubbles that appear in the fluid chamber to be easily eliminated from the system.

From the above, it is evident that the present invention provides for an advantageous design in which an inflation/deflation system can be operated with ease by a physician at the same time as she is maneuvering a dilatation catheter inside the patient's vasculature. In addition, the invention provides for a display unit for monitoring inflation times and pressures and several safety features for rapid deflation of the balloon catheter. While several particular forms of the invention have been illustrated and described, it also will be appreciated that various modifications can be made to the present invention without departing from the spirit and scope thereof.

What is claimed is:

1. An inflation/deflation system, comprising:

a catheter having an inflatable region at its distal end and an inflation lumen providing a fluid path between a proximal end of said catheter and the interior of said inflatable region;

a fluid chamber having a plunger for pressurizing a quantity of inflation fluid contained in said fluid chamber;

a conduit located between said fluid chamber and said catheter inflation lumen for directing said inflation fluid between said fluid chamber and the interior of said inflation region;

a motor drive unit coupled to the plunger to control the position of the plunger in the fluid chamber in response to control signals to thereby control the inflation fluid pressure between said fluid chamber and the interior of said inflatable region; and a control switch located near said proximal end of said catheter and remote from but in communication with said drive unit, said control switch adapted to provide control signals to the drive unit to cause the drive unit to control the movement of said plunger and thereby pressurize or depressurize said inflation fluid in said fluid chamber, and having a rapid decrease/pressure button which, when activated, controls the motor drive unit to cause fluid pressure in said inflatable region to rapidly decrease to a predetermined level.

2. The inflation/deflation system of claim 1, wherein said rapid decrease/pressure button, when activated, controls the motor drive unit to rapidly decrease pressure in said inflatable region to a negative pressure value.

3. The inflation/deflation system of claim 2 wherein:

the fluid chamber comprises a syringe having a body with the plunger movably mounted in the syringe body for altering the internal volume of the syringe body to thereby control the pressure of the fluid, the body having a first end with an outlet port formed in the first end with a tapered transition member between the body and the outlet port and the syringe is oriented vertically so that the outlet is at a higher elevation than the remainder of the syringe so that bubbles in the syringe rise to the outlet port; and the motor drive unit is connected to the plunger for moving the plunger in relation to the syringe body to alter the volume of the syringe body and the pressure of the quantity of fluid.

4. The inflation/deflation system of claim 3 further comprising:

sensing means for determining the pressure of the fluid and for generating a sensor signal indicative of the determined pressure; and means for transmitting said signal wherein the control switch comprises a display unit that receives the sensor signal from said transmitting means and displays the pressure of said fluid in response thereto.

5. The inflation/deflation system of claim 4 wherein the display unit presents pressure and pressure duration.

* * * * *